United States Patent [19]

Chu

[11] Patent Number: 4,730,000
[45] Date of Patent: Mar. 8, 1988

[54] QUINOLINE ANTIBACTERIAL COMPOUNDS

[75] Inventor: Daniel T. Chu, Vernon Hills, Ill.

[73] Assignee: Abbott Laboratories, North Chicago, Ill.

[21] Appl. No.: 784,421

[22] Filed: Oct. 7, 1985

Related U.S. Application Data

[63] Continuation of Ser. No. 597,854, Apr. 9, 1984, abandoned, which is a continuation-in-part of Ser. No. 574,227, Jan. 26, 1984, abandoned, which is a continuation-in-part of Ser. No. 514,716, Jul. 18, 1983, abandoned.

[51] Int. Cl.$^4$ .................. A61K 31/495; C07D 401/04
[52] U.S. Cl. .................................. 514/254; 514/211;
514/212; 514/218; 514/222; 514/226; 514/236;
514/314; 540/544; 540/553; 540/575; 544/54;
544/55; 544/58.6; 544/58.7; 544/121; 544/122;
544/128; 544/363; 546/156
[58] Field of Search ............... 544/363, 54, 55, 58.6,
544/58.7, 121, 122, 128; 546/156; 514/254, 314,
211, 212, 218, 222, 226, 236; 540/544, 553, 575

[56] References Cited

U.S. PATENT DOCUMENTS

| | | | |
|---|---|---|---|
| 3,149,104 | 9/1964 | Lesher et al. | 544/362 |
| 4,017,622 | 4/1977 | Minami et al. | 544/363 |
| 4,146,719 | 4/1979 | Irikura | 544/363 |
| 4,284,629 | 8/1981 | Grohe et al. | 544/279 |
| 4,292,317 | 9/1981 | Pesson | 544/363 |
| 4,382,892 | 5/1983 | Hayakawa et al. | 544/101 |
| 4,415,572 | 11/1983 | Tominaga et al. | 544/363 |
| 4,429,127 | 1/1984 | Irikura et al. | 544/363 |
| 4,439,436 | 3/1984 | Wentland et al. | 546/90 |
| 4,443,447 | 4/1984 | Gerster et al. | 544/101 |
| 4,448,962 | 5/1984 | Irikura et al. | 544/363 |
| 4,473,568 | 9/1984 | Hutt, Jr. | 544/58.6 |
| 4,499,091 | 2/1985 | Wentland et al. | 544/363 |
| 4,617,308 | 10/1986 | Mitch et al. | 514/278 |

FOREIGN PATENT DOCUMENTS

| | | | |
|---|---|---|---|
| 0009425 | 4/1980 | European Pat. Off. | |
| 0078382 | 5/1983 | European Pat. Off. | |
| 0078362 | 5/1983 | European Pat. Off. | |
| 2338325 | 2/1974 | Fed. Rep. of Germany | |
| 2362553 | 6/1974 | Fed. Rep. of Germany | 544/363 |
| 3142854 | 5/1983 | Fed. Rep. of Germany | |
| 2341146 | 2/1984 | Fed. Rep. of Germany | |
| 0128764 | 10/1981 | Japan | 544/363 |
| 1147336 | 4/1969 | United Kingdom | |
| 2034698 | 11/1972 | United Kingdom | |

OTHER PUBLICATIONS

Sato et al, "In vitro and in vivo Activity of DL-8280, a New Oxazine Derivative", *Antimicrobial Agents and Chemotherapy*, vol. 22, No. 4, pp. 548–553, Oct. 1982.

Koga et al., "SAR of Substituted Quinoline—3—Carboxylic Acids", *Journal of Medicinal Chemistry*, 1980, vol. 23, No. 12, p. 1358.

*Primary Examiner*—Glennon H. Hollrah
*Assistant Examiner*—James H. Turnipseed
*Attorney, Agent, or Firm*—Steven F. Weinstock; Martin L. Katz

[57] ABSTRACT

Quinoline compounds having the formula:

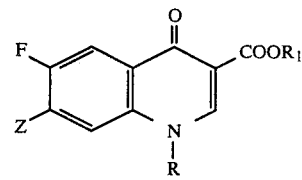

wherein R is a phenyl group or an aromatic heterocyclic group, Z is an aliphatic heterocyclic group or an amine, and $R_1$ is hydrogen or a carboxy-protecting group. The compounds here disclosed have antibacterial properties.

25 Claims, No Drawings

QUINOLINE ANTIBACTERIAL COMPOUNDS

This application is a continuation of copending application Ser. No. 597,854 filed Apr. 9, 1984 now abandoned which is a continuation-in-part of copending application Ser. No. 574,227, filed Jan. 26, 1984 now abandoned, which is a continuation-in-part of copending application Ser. No. 514,716, filed July 18, 1983 now abandoned.

This invention relates to new and useful quinoline derivatives having antibacterial properties, to compositions containing the new quinoline derivatives and to methods of treating mammalian patients with the new quinoline derivatives.

It is known that certain 7-piperazinyl-4-oxo-1,4-dihydroquinoline-3-carboxylic acids exhibit antibacterial properties. For example, U.S. Pat. No. 4,017,622 discloses certain 7-piperazinyl-4-oxo-1,4-dihydroquinoline-3-carboxylic acid derivatives wherein the 1 position substituent is alkyl, benzyl or acetyl. U.S. Pat. No. 4,292,317 discloses certain 7-piperazinyl-6-halo-4-oxo-1,4-dihydroquinoline-3-carboxylic acid derivatives wherein the 1 position substituent is methyl, ethyl, vinyl or alkyl. In U.S. Pat. No. 4,284,629, various 4-oxo-1,4-dihydroquinoline-3-carboxylic acids are disclosed in which the 1 position substituent may be cycloalkyl, although corresponding derivatives containing a 7-piperazinyl substituent are not disclosed. While the compounds of the foregoing patents may be useful in certain respects, the search continues for new quinoline derivatives which have improved properties or are otherwise useful in the treatment of bacterial infections.

The present invention relates to new 7-substituted amino-6-fluoro-1,4-dihydro-4-oxo-quinoline-3-carboxylic acids or esters having a substituted or unsubstituted phenyl radical or an aromatic heterocyclic radical in the 1 position, compositions of the new compounds together with pharmaceutically acceptable carriers, and uses of the new compounds in the treatment of bacterial infections.

The compounds of the invention can be represented by the following Formula I:

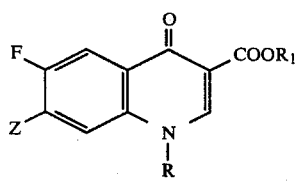
(I)

wherein R is selected from the group consisting of an aromatic heterocyclic ring having 5 to 6 atoms of which 1 or 2 atoms are selected from S, O and N and the remaining atoms being carbon atoms; substituted derivatives of the aromatic heterocyclic ring wherein the aromatic heterocyclic ring is monosubstituted with $C_1$ to $C_6$ alkyl; and a phenyl group of the formula:

(II)

wherein $R_2$ is one, two or three substituents independently selected from hydrogen, halogen, $C_1$ to $C_6$ alkyl, halo-substituted $C_1$ to $C_6$ alkyl, cyano, methylenedioxy, a group having the formula —Y—$R_3$ wherein —Y— is —O— or —S— and $R_3$ is hydrogen or $C_1$ to $C_6$ alkyl, and an amine having the formula:

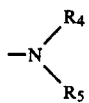

wherein $R_4$ and $R_5$ are each independently hydrogen or $C_1$ to $C_6$ alkyl.

$R_1$ is hydrogen or a carboxy-protecting group.

Z is an amino group having the formula:

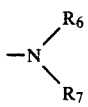

wherein $R_6$ is hydrogen or $C_1$ to $C_6$ alkyl, and $R_7$ is $C_1$ to $C_6$ alkyl, $NH_2$, mono-($C_1$-$C_4$) alkylamino or di($C_1$-$C_4$) alkylamino.

Alternatively, Z can be an aliphatic heterocyclic ring having 5 to 7 atoms and in particular, 1 or 2 hetero atoms which are selected from the group consisting of S, O and N, and combinations thereof with the remaining atoms in the aliphatic heterocyclic ring being carbon atoms. More particularly, the aliphatic heterocyclic ring has the formula:

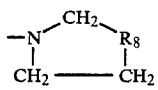

wherein $R_8$ is selected from the group consisting of $CH_2$, $(CH_2)_2$, and a group of the formula —$(CH_2)_nR_9$— wherein $R_9$ is selected from the group consisting of —S—, —O— and —N— and n is 0, 1 or 2. Also included are substituted derivatives of such aliphatic heterocyclic rings wherein the aliphatic heterocyclic ring is substituted with one, two or three of a $C_1$ to $C_6$ alkyl, an amine group having the formula:

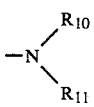

wherein $R_{10}$ and $R_{11}$ are each independently selected from the group consisting of hydrogen, $C_1$ to $C_6$ alkyl; hydroxy-substituted $C_1$ to $C_6$ alkyl, $C_1$ to $C_3$ alkylamino-substituted $C_1$ to $C_6$ alkyl, hydroxy, halogen, alkanoyl, alkanoylamido and amino-substituted $C_1$ to $C_6$ alkyl.

Representative aromatic heterocyclic groups include pyridyl, pyrazinyl, thiazoyl, furyl and thienyl.

Illustrative of aliphatic heterocyclic groups are piperazinyl groups, piperidinyl groups, piperazinyl groups, piperidinyl groups, pyrrolidinyl groups, morpholino groups, thiomorpholino groups, and homopiperazinyl groups (i.e., hexahydro-1-H-1,4-diazepin).

Representative —Y—$R_3$ groups include hydroxy, mercapto, lower alkoxy, such as methoxy, ethoxy, propoxy, etc., as well as thio analogs thereof, namely methylmercapto, ethylmercapto, etc.

As used herein, the term "halogen" refers to chloro, bromo, fluoro and iodo groups.

As used herein "$C_1$ to $C_6$ alkyl" includes both straight or branched chain alkyl. Representative of halo-substituted and hydroxy substituted $C_1$ to $C_6$ alkyl include chloromethyl, chloroethyl, chloropropyl, hydroxyethyl, etc.

As used herein, the term "alkanoyl" refers to

wherein $R_{12}$ is $C_1$ to $C_6$ alkyl.

As used herein, the term "alkanoylamido" refers to

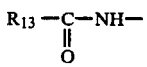

wherein $R_{13}$ is $C_1$ to $C_6$ alkyl.

As used herein, the term "carboxy-protecting group" refers to a carboxy group which has been esterified with one of the commonly used carboxylic acid protecting ester groups employed to block or protect the carboxylic acid functionality while reactions involving other functional sites of the compound are carried out. In addition, a carboxy protecting group can be used as a prodrug whereby the carboxy protecting group can be hydrolyzed enzymatically to release the biologically active parent acid. Such protected carboxy groups are noted for their ease of cleavage by hydrolytic methods to the corresponding carboxylic acid. Further, such carboxy-protecting groups can be relatively easily cleaved to yield the corresponding free carboxy group. Such carboxy-protecting groups are well known to those skilled in the art, having been extensively used in the protection of carboxyl groups in the penicillin and cephalosporin fields, as described in U.S. Pat. Nos. 3,840,556 and 3,719,667, the disclosures of which are incorporated herein by reference. Representative protecting groups include $C_1$ to $C_8$ alkyl (e.g., methyl, ethyl, tertiary butyl), benzyl and substituted derivatives thereof such as alkoxy and nitrobenzyl groups, dialkylaminoalkyl (e.g. dimethylaminoethyl), acyloxyalkyl groups such as pivaloyloxymethyl and propionyloxymethyl.

The chiral centers of the compounds of the invention may have either the "R" or "S" configuration.

Representative of the preferred compounds of the invention include 1-phenyl-6-fluoro-1,4-dihydro-4-oxo-7-(1-piperazinyl)-quinoline-3-carboxylic acid, 1-phenyl-6-fluoro-1,4-dihydro-4-oxo-7-(1-(4-methyl)-piperazinyl)-quinoline-3-carboxylic acid, 1-p-fluorophenyl-6-fluoro-1,4-dihydro-4-oxo-7-(1-piperazinyl)-quinoline-3-carboxylic acid, 1-p-fluorophenyl-6-fluoro-1,4-dihydro-4-oxo-7-(1(4-methyl)-piperazinyl)-quinoline-3-carboxylic acid, 1-p-fluorophenyl-6-fluoro-1,4-dihydro-4-oxo-7-(3-methyl-1-piperazinyl)-quinoline-3-carboxylic acid, 1-p-hydroxyphenyl-6-fluoro-1,4-dihydro-4-oxo-7-(1-piperazinyl)-quinoline-3-carboxylic acid, 1-(2,4-difluorophenyl)-6-fluoro-1,4-dihydro-4-oxo-7-(1-piperazinyl)-quinoline-3-carboxylic acid, 1-p-fluorophenyl-6-fluoro-1,4-dihydro-4-oxo-7-(1-(4-acetyl)-piperazinyl)-quinoline-3-carboxylic acid, 1-p-fluorophenyl-6-fluoro-1,4-dihydro-4-oxo-7-(3-amino-1-pyrrolidinyl)-quinoline-3-carboxylic acid, 1-p-fluorophenyl-6-fluoro-1,4-dihydro-4-oxo-7-(3-amino-4-methyl-1-pyrrolidinyl)-quinoline-3-carboxylic acid, 1-(2,4-difluorophenyl)-6-fluoro-1,4-dihydro-4-oxo-7-(3-amino-1-pyrrolidinyl)-quinoline-3-carboxylic acid, 1-(2,4-difluorophenyl)-6-fluoro-1,4-dihydro-4-oxo-7-(3-amino-4-methyl-1-pyrrolidinyl)-quinoline-3-carboxylic acid, 1-(2,4-difluorophenyl)-6-fluoro-1,4-dihydro-4-oxo-7-(4-methyl-1-piperazinyl)-quinoline-3-carboxylic acid, 1-(2,4-difluorophenyl)-6-fluoro-1,4-dihydro-4-oxo-7-(3-methyl-1-piperazinyl)-quinoline-3-carboxylic acid and 1-(2,4-difluorophenyl)-6-fluoro-1,4-dihydro-4-oxo-7-(cis-3-aminomethyl-4-chloro-1-pyrrolidinyl)-quinoline-3-carboxylic acid.

As used herein, the term "pharmaceutically acceptable salts" means the nontoxic acid addition or alkaline earth metal salts of the compounds of Formula I. These salts can be prepared in situ during the final isolation and purification of the compounds of Formula I, or by separately reacting the base or acid functions with a suitable organic or inorganic acid or base, respectively. Representative acid addition salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate, glucoheptonate, lactobionate, lauryl sulfate salts and the like. Representative alkali metal or alkaline earth metal salts include the sodium, calcium, potassium, and magnesium salts, and the like.

It has been found that the preferred compounds of the invention possess antibacterial activity against a wide spectrum of gram positive and gram negative bacteria. The compounds of the invention are therefore useful in the antibiotic treatment of susceptible bacterial infections in both humans and animals. In addition, the compounds may be used in scrub solutions, for surface inhibition of bacterial growth, e.g., on counter surfaces, and the like. Susceptible organisms generally include those gram positive and gram negative, aerobic and anaerobic organisms whose growth can be inhibited by the compounds of the invention, such as Staphylococcus, Lactobacillus, Streptococcus, Sarcina, Escherichia, Enterobacter, Klebsiella, Pseudomonas, Acinetobacter, Proteus, Citrobacter, Nisseria, Buccullus, Bacteroides, Peptococcus, Clostridium, Salmonella, Shigella, Serratia, Haemophilus, Brucella, and other organisms. In addition to exhibiting highly effective antibacterial activity, the compounds of the invention exhibit increased and improved solubility characteristics as compared with prior quinoline-3-carboxylic acid compounds in the art.

The compounds of Formula I may also be formulated into compositions together with pharmaceutically acceptable carriers for parenteral injection, for oral administration in solid or liquid form, for rectal administration, and the like.

Compositions according to the invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting, emulsifying, and dispersing agents. They may be sterilized, for example, by filtration through a bacteria-retaining filter, or by incorporating sterilizing agents in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert diluent such as sucrose, lactose or starch. Such dosage forms can also comprise, as in normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides such inert diluents, compositions can also include adjuvants, such as wetting agents, emulsifying and suspending agents, and sweetening, flavoring and perfuming agents.

Compositions for rectal administration are preferably suppositories which may contain, in addition to the active substance, excipients such as cocoa butter or a suppository wax.

Actual dosage levels of active ingredient in the compositions of the invention may be varied so as to obtain an amount of active ingredient effective to achieve antibacterial activity in accordance with the desired method of administration. The selected dosage level therefore depends upon the nature of the active compound administered, the route of administration, the desired duration of treatment and other factors. Generally, daily dosage levels of the compounds of Formula I of about 0.1 to about 750, more preferably about 0.25 to about 500 and most preferably about 0.5 to about 300 mg. of active ingredient per kg. of body weight are effective when administered orally to a mammalian patient suffering from an infection caused by a susceptible organism. If desired, the daily dose may be divided into multiple doses for administration, e.g., two to four times per day.

The compounds may be prepared in accordance with the following reaction scheme:

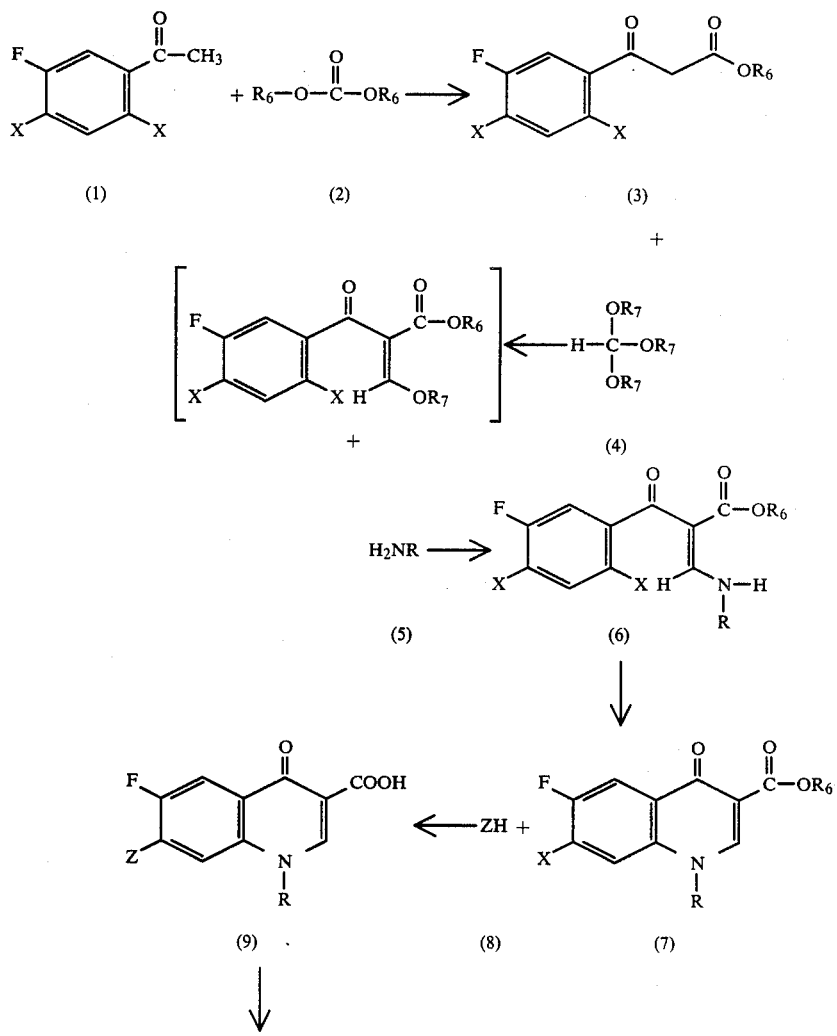

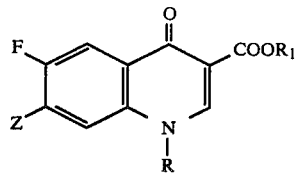

(10)

In accordance with the foregoing reaction scheme, 2,4-dihalo-5-fluoro-acetophenone (1) is reacted with a dialkoxycarbonate (2) in the presence of a strong base to obtain the corresponding $\beta$-ketoester (3). In the 2,4-dihalo-5-fluoro-acetophenone (1), X may be a chloro or fluoro group. In the dialkoxycarbonate (2), $R_6$ may be an alkyl group of, for example, 1 to 10 carbon atoms, but is preferably lower alkyl, such as ethyl. Suitable bases include the metal hydrides, such as sodium hydride, potassium hydride and the like, as well as metal alkoxides in alcohol, such as sodium ethoxide in ethanol. The presently preferred base for this purpose is sodium hydride. Formation of the $\beta$-ketoester (3) is facilitated by reacting the acetophenone (1) with the dialkoxycarbonate (2) at elevated temperatures, such as from about 20° C. to about 120° C., and preferably from about 30° C. to about 90° C. until completion of the reaction. The $\beta$-ketoester may then be separated from the reaction mixture in a conventional manner.

The $\beta$-ketoester (3) is then treated with a trialkylorthoformate (4) in the presence of an acid anhydride, preferably acetic anhydride, followed by reaction with substituted or unsubstituted aniline or other aromatic heterocyclic amine (5) to obtain the enaminoketoester (6). In the trialkylorthoformate (4), $R_7$ may be an alkyl group of, for example, from 1 to 10 carbon atoms, but is preferably lower alkyl, such as ethyl. Reaction with the trialkylorthoformate is preferably conducted at elevated temperatures, such as from about 50° C. to about 150° C., preferably from about 100° C. to about 140° C., to obtain an oily liquid as an unisolated intermediate (shown in brackets in the reaction scheme). Reaction of the latter with the substituted or unsubstituted aniline or aromatic heterocyclic amine (5) is preferably conducted in an appropriate aprotic on nonaprotic solvent, preferably methylene chloride or tetrahydrofuran, and may be conducted at room or suitable elevated temperature, as desired.

The enaminoketoester (6) is then cyclized, such as by treatment with a strong base as defined above, preferably sodium hydride, to obtain the 1-aryl-1,4-dihydro-4-oxo-quinoline-3-carboxylic acid ester (7). Cyclization is conducted in the presence of an aprotic solvent, such as dimethoxyethane, dimethylformamide, tetrahydrofuran or chlorobenzene, and is preferably conducted at temperatures of about 20° C. to about 145° C., more preferably at the reflux temperature of the solvent employed.

The ester (7) is subjected to hydrolysis, such as by treatment with sodium hydroxide, to form the free acid (7) ($R_6$=H), followed by displacement of the 7-halo radical with substituted or unsubstituted piperazine or other heterocyclic amines (8) as described above by techniques known in the art to obtain the desired 1-aryl-6-fluoro-7-substituted amino-1,4-dihydroxy-4-oxo-quinoline-3-carboxylic acid (9).

The 1-aryl-6-fluoro-7-substituted amino-1,4-dihydro-4-oxo-quinoline-3-carboxylic acid (9) can then be converted into the corresponding ester (10), if desired, by conventional esterification procedures, such as by treating the free acid (9) with the appropriate alcohol in the presence of an acid catalyst, by converting the free acid (9) into the corresponding acid chloride followed by displacement of the chloro radical with the appropriate alcohol, or by treating the sodium salt of the acid (9) with a suitable reactive halide, such as chloro-methyl-pivalate in dimethoxyethane to obtain, for example, the pivaloyloxymethyl ester (1) wherein $R_2$ is —CH$_2$OCOC(CH$_3$)$_3$.

The foregoing may be better understood from the following examples, which are presented for purposes of illustration and are not intended to limit the scope of the inventive concepts. As used in the following examples, the references to compounds, such as (1), (2), (3), etc., and to substituents, such as R, $R_1$, $R_2$, etc., refer to the correspondings and substituents in the foregoing scheme.

EXAMPLE 1

1-phenyl-6-fluoro-1,4-dihydro-4-oxo-7(1-piperazinyl)-quinoline-3-carboxylic acid (a) To a cold solution of 20.5 g. 2,4-dichloro-5-fluoroacetophenone in 300 ml. diethylcarbonate is slowly added 8.2 g. 60% sodium hydride-in-oil suspension. The mixture is heated at 80° C. for 1½ hours, then poured into 700 ml. ice cold water solution containing 25 ml. acetic acid. The mixture is extracted with three 400 ml. portions of ether. The organic phase is dried over MgSO$_4$, evaporated and the obtained liquid is distilled at 111° C. at 0.7 mm. of Hg. pressure to give 22.2 g. of (3) wherein $R_6$=C$_2$H$_5$.

(b) A solution of 15.18 g. of $\beta$-ketoester (3) ($R_6$=C$_2$H$_5$) in 14 ml. of triethylorthoformate and 35 ml. of acetic anhydride is heated at 135° C. for 1½ hours with the removal of the ethyl acetate formed during the reaction. The solution is evaporated under reduced pressure to a mobile oil. The oil is then dissolved in 150 ml. of methylene chloride and 7.5 ml. of aniline is added into the solution. After 1 hour, the solution is evaporated to dryness and crystallized from 200 ml. of hexane and 5 ml. of ether yielding (6), wherein $R_6$=C$_2$H$_5$ and R=phenyl in 89% yield, m.p. 96°-97° C.

(c) To a cold solution of 13.9 g. of the preceding product (6), $R_6$=C$_2$H$_5$, R=phenyl in 140 ml. dimethoxymethane (DME) is slowly added 1.49 g. of a 60% sodium hydride-in-oil suspension. The mixture is refluxed for 4½ hours and is cooled and diluted with water to a volume of 1.5 liters. The mixture is then filtered and the solid is washed with a 1:1 hexane/ether solution to obtain 10.4 g. of (7) wherein $R_6$=C$_2$H$_5$ and R=phenyl in 81% yield.

(d) To a suspension of 5.4 g. of (7) ($R_6$=C$_2$H$_5$, R=phenyl) in 30 ml. THF is added a sodium hydroxide solution (0.73 g. in 20 ml. H$_2$O). The mixture is heated at 80° C. for 1 hour resulting in a clear solution which is evaporated under reduced pressure to dryness. The solid is dissolved in 200 ml. H₂O, and 2 ml. acetic acid is added. The resulting precipitate is filtered and washed with cold water, crystallized from dimethylformamide (DMF) to produce 4.6 g. of 7-chloro-1-phenyl-6-fluoro-1,4-dihydro-4-oxo-quinoline-3-carboxylic acid (7) (R₆=hydrogen, R=phenyl), m.p. 271°-273° C.

(e) To a solution of 1.25 g. of 7-chloro-1-phenyl-6-fluoro-1,4-dihydro-4-oxo-quinoline-3-carboxylic acid in 15 ml. of 1-methyl-2-pyrrolidinone at 115° C. is added 2 ml. piperazine. After stirring at 100° C. for 20 hours, the solvent is removed by reduced pressure to dryness. Ethanol is added to the residue and the resulting mixture is filtered and washed with ether and then washed with very small amounts of cold water. The resulting dried solid is suspended in 30 ml. H₂O and 2.35 ml. 1N HCl is added to and warmed to dissolve. Removal of the solvent under reduced pressure gives 835 mg. hydrochloride salt of 1-phenyl-6-fluoro-1,4-dihydro-4-oxo-7-(1-piperazinyl)-quinoline-3-carboxylic acid (9) (R=phenyl,

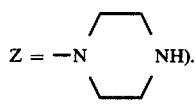

To the hydrochloride salt is added one molar equivalent of an aqueous solution of sodium hydroxide, and the resulting precipitate is filtered to obtain 1-phenyl-6-fluoro-1,4-dihydro-4-oxo-7-(1-piperazinyl) quinoline-3-carboxylic acid.

(f) Alternately, the title compound is prepared as follows: To a suspension of 5.87 g. of compound (7) (R₆=H, R=phenyl; product of 1(d)) in 40 ml. 1-methyl-2-pyrrolidinone at 120° C. under nitrogen atmosphere is added 9.5 ml. of N-carboethoxy-p-erazine. After 20 hours, the solvent is removed under reduced pressure, and the residue is suspended in 150 ml. ethanol and refluxed for ½ hour. The reaction mixture is then cooled and filtered. The resulting solid is washed with cold ethanol and water to obtain 6.15 g. of compound (9) (R=phenyl,

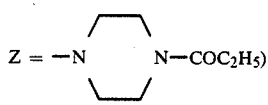

in 87% yield.

To a suspension of 5.5 g. of the preceding compound (9) (R=phenyl,

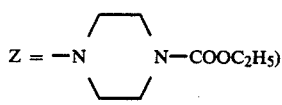

in 25 ml. of ethanol at 80° C. is added 50 ml. of 10% NaOH solution. The solution is heated at 80° C. for 6 hours. The solvent is removed and the solid is dissolved in 100 ml. water. The pH to the solution is adjusted to pH 7 by the addition of 10% acetic acid. The precipitate is filtered and washed with cold water yielding 4.26 of 1-phenyl-6-fluoro-1,4-dihydro-4-oxo-7-(1-piperazinyl) quinoline-3-carboxylic acid (9) (R=phenyl,

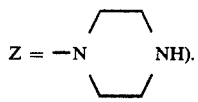

EXAMPLE 2

1-phenyl-6-fluoro-1,4-dihydro-4-oxo-7-(1-(4-methyl)-piperazinyl)quinoline-3-carboxylic acid The procedure of Example 1 can be repeated, replacing piperazine in Example 1(e) with N-methylpiperazine to obtain 1-phenyl-6-fluoro-1,4-dihydro-4-oxo-7(1-(4-methyl)-piperazinyl)-quinoline-3-carboxylic acid (9) (R=phenyl,

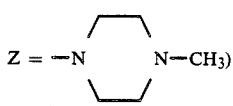

and its hydrochloride salt.

EXAMPLE 3

1-phenyl-6-fluoro-1,4-dihydro-4-oxo-7-(1-(4-ethyl)-piperazinyl)quinoline-3-carboxylic acid The procedure of Example 1 can be repeated, replacing piperazine in Example 1(e) with N-ethylpiperazine to obtain the 1-phenyl-6-fluoro-1,4-dihydro-4-oxo-7-(1-(4-ethyl)-piperazinyl)-quinoline-3-carboxylic acid (9) (R=phenyl,

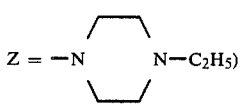

and its hydrochloride salt.

EXAMPLE 4

1-p-fluorophenyl-6-fluoro-1,4-dihydro-4-oxo-(1-piperazinyl)quinoline-3-carboxylic acid (a) In the described fashion as Example 1(b), replacing aniline with p-fluoroaniline, one can obtain the enaminoketoester (6) (R₆=C₂H₅, R=p-fluorophenyl) in 78% yield, m.p. 108° C.

(b) By following the Example 1(c) and 1(d), the preceding compound (6) (R₆=C₂H₅, R=p-fluorophenyl) can yield 7-chloro-1-p-fluorophenyl-6-fluoro-1,4-dihydro-4-oxo-quinoline-3-carboxylic acid (7) R₆=H, R=p-fluorophenyl).

(c) In the described fashion as Example 1(e), the above acid (7) R₆=H, R=p-fluorophenyl), after reacting with the piperazine, can give the desired 1-p-fluorophenyl-6-fluoro-1,4-dihydro-4-oxo-7-(1-piperazinyl)-quinoline-3-carboxylic acid (9)

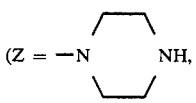

R=p-fluorophenyl) and its hydrochloride salt.

EXAMPLE 5

1-(p-difluorophenyl)-6-fluoro-1,4-dihydro-4-oxo-7(1-(4-methyl)-piperazinyl)quinoline-3-carboxylic acid In the described fashion as Example 1(e), replacing piperazine with N-methylpiperazine, the acid (7) (R$_6$=H, R=p-fluorophenyl in Example 4(b) can yield the described 1-p-fluorophenyl-6-fluoro-1,4-dihydro-4-oxo-7-(1-(4-methyl)-piperazinyl)quinoline-3-carboxylic acid (9)

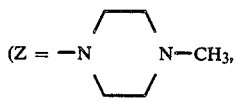

R=p-fluorophenyl and its hydrochloride salt.

EXAMPLE 6

1-(2,4-difluorophenyl-6-fluoro-1,4-dihydro-4-oxo-(1-piperazinyl)quinoline-3-carboxylic acid (a) In the described fashion as Example 1(b), replacing aniline with 2,4-difluoroaniline, one can obtain the enaminoketoester (6) (R$_6$=C$_2$H$_5$, R=2,4-difluorophenyl) in 64% yield.

(b) By following Example 1(c) and 1(d), the preceding compound (6) (R$_6$=C$_2$H$_5$, R=2,4-difluorophenyl) can yield 7-chloro-1-(2,4-difluorophenyl)-6-fluoro-1,4-dihydro-4-oxo-quinoline-3-carboxylic acid (7) (R$_6$=H, R=2,4-difluorophenyl).

(c) In the described fashion as Example 1(e), the above acid (7) (R$_6$=H, R=2,4-difluorophenyl), after reacting with piperazine, can give the described 1-(2,4-difluorophenyl)-6-fluoro-1,4-dihydro-4-oxo-7-(piperazinyl)quinoline-3-carboxylic acid (9)

R=2,4-difluorophenyl) and its hydrochloride salt.

EXAMPLE 7

1-(2,4-difluorophenyl)-6-fluoro-1,4-dihydro-4-oxo-7-(1-(4-methyl)-piperazinyl)quinoline-3-carboxylic acid In the described fashion as Example 1(e), replacing piperazine with N-methylpiperazine, the acid (7) (R$_6$=H, R=2,4-difluorophenyl) in Example 6(b) can yield the desired 1-(2,4-difluorophenyl)-6-fluoro-1,4-dihydro-4-oxo-7-(1-(4-methyl)-piperazinyl)quinoline-3-carboxylic acid (9)

R=2,4-difluorophenyl) and its hydrochloride salt.

EXAMPLE 8

1-p-methoxyphenyl-6-fluoro-1,4-dihydro-4-oxo-(1-piperazinyl)quinoline-3-carboxylic acid (a) In the described fashion as Example 1(b), replacing aniline with p-methoxyaniline, one can obtain the enaminoketoester (6) (R$_6$=C$_2$H$_5$, R=p-OCH$_3$-phenyl) in 77% yield (m.p. 105° C.).

(b) By following the Example 1(c) and 1(d), the preceding compound (6) (R$_6$=C$_2$H$_5$, R=p-methoxyphenyl) can yield 7-chloro-1-p-methoxyphenyl-6-fluoro-1,4-dihydro-4-oxo-quinoline-3-carboxylic acid (7) (R$_6$=H, R=p-methoxyphenyl).

(c) In the described fashion as Example 1(e), the above acid (7) (R$_6$=H, R=p-methoxyphenyl) after reacting with piperazine can give the desired 1-p-methoxyphenyl-6-fluoro-1,4-dihydro-4-oxo-7-(1-piperazinyl)-quinoline-3-carboxylic acid (9)

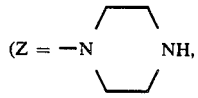

R=p-methoxyphenyl) and its hydrochloride salt.

EXAMPLE 9

1-p-methoxyphenyl-6-fluoro-1,4-dihydro-4-oxo-7-(1-(4-methyl)-piperazinyl)quinoline-3-carboxylic acid In the described fashion as Example 1(e), replacing piperazine with N-methylpiperazine, the acid (7) (R$_6$=H, R=p-methoxyphenyl) in Example 8(b) can yield the described 1-p-methoxyphenyl-6-fluoro-1,4-dihydro-4-oxo-7-(1-methyl)-piperazinyl)quinoline-3-carboxylic acid (9)

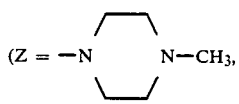

R=p-methoxyphenyl and its hydrochloride salt.

EXAMPLE 10

1-p-methylphenyl-6-fluoro-1,4-dihydro-4-oxo-7-(piperazinyl)quinoline-3-carboxylic acid (a) In the described fashion as Example 1(b), replacing aniline with p-methylaniline, one can obtain the enaminoketoester (6) (R$_6$=C$_2$H$_5$, R=p-methylphenyl) in 80% yield (m.p. 115.5° C.).

(b) By following the Example 1(c) and 1(d), the preceding compound (6) (R$_6$=C$_2$H$_5$, R=p-methylphenyl) can yield 7-chloro-1-p-methylphenyl-6-fluoro-1,4-dihydro-4-oxo-quinoline-3-carboxylic acid (7) (R$_6$=H, R=p-methyl-phenyl).

(c) In the described fashion as Example 1(e), the above acid (7) (R$_6$=H, R=p-methylphenyl), after reacting with piperazine, can give the desired 1-p-methylphenyl-6-fluoro-1,4-dihydro-4-oxo-7-(1-piperazinyl)-quinoline-3-carboxylic acid (9)

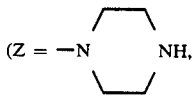

R=p-methylphenyl) and its hydrochloride salt.

EXAMPLE 11

1-p-methylphenyl-6-fluoro-1,4-dihydro-4-oxo-7-(1-(4-methyl)-piperazinyl)quinoline-3-carboxylic acid In the described fashion as Example 1(e), replacing piperazine with N-methylpiperazine, the acid (7) ($R_6$=H, R-p-methylphenyl) in Example 10(b) can yield the desired 1-p-methylphenyl-6-fluoro-1,4-dihydro-4-oxo-7-(1-(4-methyl)-piperazinyl)quinoline-3-carboxylic acid (9)

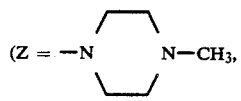

R=p-methylphenyl) and its hydrochloride salt.

EXAMPLE 12

1-p-hydroxyphenyl-6-fluoro-1,4-dihydro-4-oxo-(1-piperazinyl)quinoline-3-carboxylic acid (a) In the described fashion as Example 1(b), replacing aniline with p-hydroxyaniline, one can obtain the enaminoketoester (6) ($R_6$=$C_2H_5$, R=p-hydroxyphenyl) in 84% yield.

(b) By following the Example 1(c) and 1(d), the preceding compound (6) ($R_6$=$C_2H_5$, R=p-hydroxyphenyl) can yield 7-chloro-1-p-hydroxyphenyl-6-fluoro-1,4-dihydro-4-oxo-quinoline-3-carboxylic acid (7) ($R_6$=H, R=p-hydroxyphenyl) in good yield.

(c) In the described fashion as Example 1(e), the above acid (7) ($R_6$=H, R=p-hydroxyphenyl) after reacting with piperazine can give the desired 1-p-hydroxyphenyl-6-fluoro-1-4-dihydro-4-oxo-7-(1-piperazinyl)-quinoline-3-carboxylic acid (9)

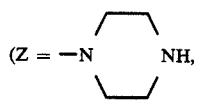

R=p-hydroxyphenyl) and its hydrochloride salt.

EXAMPLE 13

1-p-hydroxyphenyl-6-fluoro-1,4-dihydro-4-oxo-7(1-(4-methyl)-piperazinyl)quinoline-3-carboxylic acid In the described fashion as Example 1(e), replacing piperazine with N-methylpiperazine, the acid (7) ($R_6$=H, R=p-hydroxyphenyl) in Example 12(b) can yield the desired 1-p-hydroxyphenyl-6-fluoro-1,4-dihydro-4-oxo-7-(1-(4-methyl)-piperazinyl)quinoline-3-carboxylic acid (9)

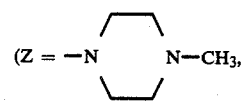

R=p-hydroxyphenyl) and its hydrochloride salt.

EXAMPLE 14

1-o-fluorophenyl-6-fluoro-1,4-dihydro-4-oxo-(1-piperazinyl)quinoline-3-carboxylic acid (a) In the described fashion as Example 1(b), replacing aniline with o-fluoroaniline, one can obtain the enaminoketoester (7) ($R_6$=$C_2H_5$, R=o-fluorophenyl) in 78.8% yield (m.p. 90°-92° C.).

(b) By following the Example 1(c) and 1(d), the preceding compound (6) ($R_6$=$C_2H_5$, R=o-fluorophenyl) can yield 7-chloro-1-o-fluorophenyl-6-fluoro-1,4-dihydro-4-oxo-quinoline-3-carboxylic acid (7) ($R_6$=H, R=o-fluoro-phenyl).

(c) In the described fashion as Example 1(e), the above acid (7) ($R_6$=H, R=o-fluorophenyl) after reacting with piperazine can give the desired 1-o-fluorophenyl-6-fluoro-1,4-dihydro-4-oxo-7-(1-piperazinyl)-quinoline-3-carboxylic acid (9)

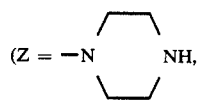

R=o-fluorophenyl) and its hydrochloride salt.

EXAMPLE 15

1-o-fluorophenyl-6-fluoro-1,4-dihydro-4-oxo-7(1-(4-methyl)-piperazinyl)quinoline-3-carboxylic acid In the described fashion as Example 1(e), replacing piperazine with N-methylpiperazine, the acid (7) ($R_6$=H, R=o-fluorophenyl) in Example 14(b) can yield the desired 1-o-fluorophenyl-6-fluoro-1,4-dihydro-4-oxo-7-(1-(4-methyl)-piperazinyl)quinoline-3-carboxylic acid (9)

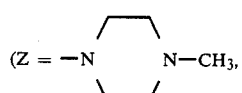

R=o-fluorophenyl) and its hydrochloride salt.

EXAMPLE 16

1-m-fluorophenyl-6-fluoro-1,4-dihydro-4-oxo-(1-piperazinyl)quinoline-3-carboxylic acid (a) In the described fashion as Example 1(b), replacing aniline with m-fluoroaniline, one can obtain the enaminoketoester (6) (R=$C_2H_5$, R=m-fluorophenyl) in 68.5% yield (m.p. 103°-104° C.).

(b) By following the Example 1(c) and 1(d), the preceding compound (6) ($R_6$=$C_2H_5$, R=m-fluorophenyl) can yield 7-chloro-1-m-fluorophenyl-6-fluoro-1,4-dihydro-4-oxo-quinoline-3-carboxylic acid (7) ($R_6$=H, R=m-fluoro-phenyl).

(c) In the described fashion as Example 1(e), the above acid (7) (R=H, R=m-fluorophenyl) after reacting with piperazine can give the described 1-m-fluorophenyl-6-fluoro-1,4-dihydro-4-oxo-7-(1-piperazinyl)-quinoline-3-carboxylic acid (9)

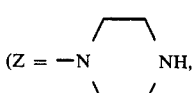

R=m-fluorophenyl) and its hydrochloride salt.

EXAMPLE 17

1-p-cyanophenyl-6-fluoro-1,4-dihydro-4-oxo-(1-piperazinyl)quinoline-3-carboxylic acid (a) In the described fashion as Example 1(b), replacing aniline with p-cyanoaniline, one can obtain the enaminoketoester (6) ($R_6=C_2H_5$, R=p-cyanophenyl) in 91.2% yield.

(b) By following the Example 1(c) and 1(d), the preceding compound (6) ($R_6=C_2H_5$, R=p-cyanophenyl) can yield 7-chloro-1-p-cyanophenyl-6-fluoro-1,4-dihydro-4-oxo-quinoline-3-carboxylic acid (7) ($R_6=H$, R=p-cyanophenyl).

(c) In the described fashion as Example 1(e), the above acid (7) ($R_6=C_2H_5$, R=p-cyanophenyl), after reacting with piperazine, can give the desired 1-p-cyanophenyl-6-fluoro-1,4-dihydro-4-oxo-7-(1-piperazinyl)-quinoline-3-carboxylic acid (9)

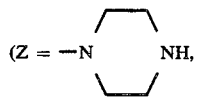

R=p-cyanophenyl) and its hydrochloride salt.

EXAMPLE 18

1-p-cyanophenyl-6-fluoro-1,4-dihydro-4-oxo-7-(1-(4-methyl)-piperazinyl)quinoline-3-carboxylic acid In the described fashion as Example 1(e), replacing piperazine with N-methylpiperazine, the acid (7) ($R_6=H$, R=p-cyanophenyl) in example 17(b) can yield the described 1-p-cyanophenyl-6-fluoro-1,4-dihydro-4-oxo-7-(1-(4-methyl)-piperazinyl)quinoline-3-carboxylic acid (9)

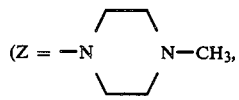

R=p-cyanophenyl) and its hydrochloride salt.

EXAMPLE 19

1-4-pyridyl-6-fluoro-1,4-dihydro-4-oxo-(1-piperazinyl)-quinoline-3-carboxylic acid (a) In the described fashion as Example 1(b), replacing aniline with 4-aminopyridine, one can obtain the enaminoketoester (6) ($R_6=C_2H_5$), R=4-pyridyl) in 70% yield as oil.

(b) By following the Example 1(c) and 1(d), the preceding compound (6) ($R_6=C_2H_5$, R=4-pyridyl) can yield 7-chloro-1-(4-pyridyl)-6-fluoro-1,4-dihydro-4-oxo-quinoline-3-carboxylic acid (7) ($R_6=H$, R=4-pyridyl).

(c) In the described fashion as Example 1(e), the above acid (7) ($R_6=H$, R=4-pyridyl) after reacting with piperazine can give the desired 1-4-pyridyl-6-fluoro-1,4-dihydro-4-oxo-7-(1-piperazinyl)-quinoline-3-carboxylic acid (9) (R=4-pyridyl,

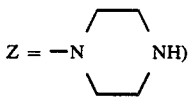

and its hydrochloride salt.

EXAMPLE 20

1-4-pyridyl-6-fluoro-1,4-dihydro-4-oxo-7-(1-(4-methyl)-piperazinyl)quinoline-3-carboxylic acid In the described fashion as Example 1(e), replacing piperazine with N-methylpiperazine, the acid (7) ($R_6=H$, R=4-pyridyl) in Example 19(b) can yield the desired 1-4-pyridyl-6-fluoro-1,4-dihydro-4-oxo-7-(1-(4-methyl)-piperazinyl)quinoline-3-carboxylic acid (9)

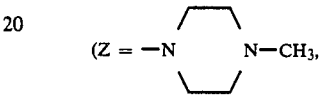

R=4-pyridyl).

EXAMPLE 21

1-3-pyridyl-6-fluoro-1,4-dihydro-4-oxo-(1-piperazinyl)-quinoline-3-carboxylic acid (a) In the described fashion as Example 1(b), replacing aniline with 3-aminopyridine, one can obtain the enaminoketoester (6) ($R_6=C_2H_5$, R=3-pyridyl) in 80% yield.

(b) By following the Example 1(c) and 1(d), the preceding compound (6) ($R_6=C_2H_5$, R=3-pyridyl) can yield 7-chloro-1-(3-pyridyl)-6-fluoro-1,4-dihydro-4-oxo-quinoline-3-carboxylic acid (7) ($R_6=H$, R=3-pyridyl).

(c) In the described fashion as Example 1(e), the above acid (7) ($R_6=H$, R=3-pyridyl) after reacting with piperazine can give the desired 1-(3-pyridyl)-6-fluoro-1,4-dihydro-4-oxo-7-(1-piperazinyl)-quinoline-3-carboxylic acid (9) (R=3-pyridyl,

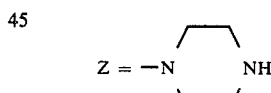

and its hydrochloride salt.

EXAMPLE 22

1-3-pyridyl-6-fluoro-1,4-dihydro-4-oxo-7-(1(4-methyl)-piperazinyl)quinoline-3-carboxylic acid In the described fashion as Example 1(e), replacing piperazine with N-methylpiperazine, the acid (7) ($R_6=H$, R=3-pyridyl) in Example 21(b) can yield the desired 1-3-pyridyl-6-fluoro-1,4-dihydro-4-oxo-7-(1-(4-methyl)-piperazinyl)quinoline-3-carboxylic acid in good yield (9)

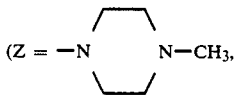

R=3-pyridyl).

EXAMPLE 23

In similar fashion as Example 1, the use of various substituted anilines and other amino aromatic compounds in place of aniline and the use of appropriate N-substituted piperazine, the following additional compounds and their hydrochloride salts can be made as summarized in Table I.

TABLE I

| Aniline Replacement | Piperazine Substituent | Compound (9) Obtained Z | R |
|---|---|---|---|
| 1. p-nitroaniline | CH$_3$ | N—methyl-piperazinyl | p-nitrophenyl |
| 2. p-nitroaniline | H | piperazinyl | p-nitrophenyl |
| 3. p-dimethylamino-aniline | H | piperazinyl | p-dimethyl-aminophenyl |
| 4. p-aminobenzoic acid | H | piperazinyl | p-carboxylphenyl |
| 5. p-trifluoro-methylaniline | H | piperazinyl | p-trifluoro-methylphenyl |
| 6. 4-chloro-aniline | H | piperazinyl | 4-chlorophenyl |
| 7. 4-chloro-aniline | CH$_3$ | N—methyl-piperazinyl | 4-chloro-phenyl |
| 8. 2-chloro-4-fluoraniline | H | piperazinyl | 2-chloro-4-fluorophenyl |
| 9. 2-fluoro-4-hydroxyaniline | H | piperazinyl | 2-fluoro-4-hydroxyphenyl |
| 10. 3,4-methylene-dioxyaniline | H | piperazinyl | p-fluorophenyl |
| 11. 2,4-dihydroxy-aniline | H | piperazinyl | 2,4-hydroxyphenyl |
| 12. p-methylmercapto-aniline | CH$_3$ | N—methyl-piperazinyl | p-methyl-mercapto |
| 13. p-methylmercapto-aniline | H | piperazinyl | p-methyl-mercapto |
| 14. 3-fluoro-4-hydroxyaniline | H | piperazinyl | 3-fluoro-4-hydroxyphenyl |
| 15. 3-chloro-4-hydroxyaniline | H | piperazinyl | 3-chloro-4-hydroxyphenyl |
| 16. 3,4-methylene-dioxyaniline | H | piperazinyl | 3,4-methylene-dioxyphenyl |
| 17. 3,4-methylene-dioxyaniline | H | N—methyl-piperazinyl | 3,4-methylene-dioxyphenyl |

EXAMPLE 24

In similar fashion to that described in Example 1, the use of various aromatic heterocyclic amines in place of aniline and the use of appropriate N-substituted piperazines can result in the following additional compounds and their hydrochloride salts as summarized in Table II.

TABLE II

| Aniline Replacement | Piperazine Substituent | Compound (9) Obtained Z | R |
|---|---|---|---|
| 1. 4-amino-2-methyl-pyridine | H | piperazinyl | 3-methyl-4-pyridinyl |
| 2. 3-pyrazine | H | piperazinyl | 3-pyrazinyl |
| 3. 3-pyrazine | CH$_3$ | N—methyl-piperazinyl | 3-pyrazinyl |
| 4. 2-aminothiazole | H | piperazinyl | 2-thiazolyl |
| 5. 1,2,4-triazole | H | piperazinyl | triazolyl |
| 6. 3-aminofuran | H | piperazinyl | 3-furyl |
| 7. 3-aminothiophene | H | piperazinyl | 3-thienyl |

EXAMPLE 25

1-p-fluorophenyl-6-fluoro-1,4-dihydro-4-oxo-7-thiomorpholino-quinoline-3-carboxylic acid To a solution of 3.36 g of 7 chloro-1-p-fluoro-phenyl-6-fluoro-1,4-dihydro-4-oxo-quinoline-3-carboxylic acid (the product of Example 4(b)) in 35 ml of 1-methyl-2-pyrrolidinone at 115° C. is added 4.13 g of thiomorpholine. After stirring at 115° C. for 20 hours, the solvent is removed by reduced pressure to dryness. Methanol is added to the residue and the resulting mixture is filtered and washed with ethylacetate and then washed with water. The solid is dried, yielding 2.51 g 1-p-fluorophenyl-6-fluoro-1,4-dihydro-4-oxo-7-thiomorpholino-quinoline-3-carboxylic acid (9)

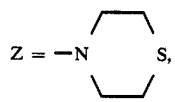

R=p-fluorophenyl) in 62% yield.

EXAMPLE 26

1-phenyl-6-fluoro-1,4-dihydro-4-oxo-7-thiomorpholino-quinoline-3-carboxylic acid The procedure of Example 25 can be repeated, replacing the 7-chloro-1-p-fluorophenyl-6-fluoro-1,4-dihydro-4-oxo-quinoline-3-carboxylic acid with 7-chloro-1-phenyl-6-fluoro-1,4-dihydro-4-oxo-quinoline-3-carboxylic acid (product of Example 1(d)) to obtain 1-phenyl-6-fluoro-1,4-dihydro-4-oxo-7-thiomorpholino-quinoline-3-carboxylic acid (9)

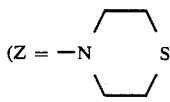

R=phenyl).

EXAMPLE 27

1-p-methoxyphenyl-6-fluoro-1,4-dihydro-4-oxo-7-thiomorpholino-quinoline-3-carboxylic acid In the described fashion as Example 25, replacing the 7-chloro-1-p-fluorophenyl-6-fluoro-1,4-dihydro-4-oxo-quinoline-3-carboxylic acid with 7-chloro-1-p-methoxyphenyl-6-fluoro-1,4-dihydro-4-oxo-quinoline-3-carboxylic acid (product of Example 8(b)) one can obtain the 1-p-methoxyphenyl-6-fluoro-1,4-dihydro-4-oxo-7-thiomorpholino-quinoline-3-carboxylic acid (9)

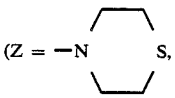

R=p-methoxyphenyl).

EXAMPLE 28

1-p-hydroxyphenyl-6-fluoro-1,4-dihydro-4-oxo-7-thiomorpholino-quinoline-3-carboxylic acid The procedure of Example 25 can be repeated, replacing the 7-chloro-1-p-fluorophenyl-6-fluoro-1,4-dihydro-4-oxo-quinoline-3-carboxylic acid with 7-chloro-1-p-hydroxy-phenyl-6-fluoro-1,4-dihydro-4-oxo-quinoline-3-carboxylic acid (product of Example 12(b)) to obtain 1-p-hydroxyphenyl-6-fluoro-1,4-dihydro-4-oxo-7-thiomorpholino-quinoline-3-carboxylic acid (9)

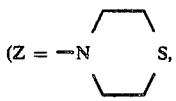

R=p-hydroxyphenyl).

EXAMPLE 29

1-phenyl-6-fluoro-1,4-dihydro-4-oxo-7-morpholino-quinoline-3-carboxylic acid

To a solution of 2.5 g of 7-chloro-1-phenyl-6-fluoro-1,4-dihydro-4-oxo-quinoline-3-carboxylic acid (product of Example 1(d)) in 30 ml of methyl-2-pyrrolidinone at 115° C. is added in 4 ml of morpholine. After stirring at 115° C. for 20 hours, the solvent is removed by reduced pressure to dryness. Ethanol is added to the residue and the resulting mixture is filtered and washed with ethanol and then water. The solid is dried, yielding 1.98 g 1-phenyl-6-fluoro-1,4-dihydro-4-oxo-7-morpholino-quinoline-3-carboxylic acid (9)

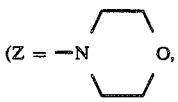

R=phenyl).

EXAMPLE 30

1-p-fluorophenyl-6-fluoro-1,4-dihydro-4-oxo-7-morpholino-quinoline-3-carboxylic acid The procedure of Example 29 can be repeated, replacing the 7-chloro-1-phenyl-6-fluoro-1,4-dihydro-4-oxo-quinoline-3-carboxylic acid with 7-chloro-1-p-fluorophenyl-6-fluoro-1,4-dihydro-4-oxo-quinoline-3-carboxylic acid (product of Example 4(b)) to obtain 1-p-fluorophenyl-6-fluoro-1,4-dihydro-4-oxo-7-morpholino-quinoline-3-carboxylic acid (9)

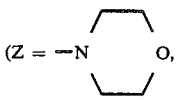

R=p-fluorophenyl).

EXAMPLE 31

1-p-hydroxyphenyl-6-fluoro-1,4-dihydro-4-oxo-7-morpholino-quinoline-3-carboxylic acid In the described fashion as Example 29, replacing the 7-chloro-1-phenyl-6-fluoro-1,4-dihydro-4-oxo-quinoline-3-carboxylic acid with 7-chloro-1-p-hydroxyphenyl-6-fluoro-1,4-dihydro-4-oxo-quinoline-3-carboxylic acid (product of Example 12(b)) one can obtain the 1-p-hydroxyphenyl-6-fluoro-1,4-dihydro-4-oxo-7-morpholino-quinoline-3-carboxlyic acid (9)

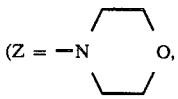

R=p-hydroxyphenyl).

EXAMPLE 32

1-phenyl-6-fluoro-1,4-dihydro-4-oxo-7-(3-amino-1-pyrrolidinyl)quinoline-3-carboxylic acid (a) To a solution of 1.5 g 7-chloro-1-phenyl-6-fluoro-1,4-dihydro-4-oxo-quinoline-3-carboxylic acid (product of Example 1(d)) in 20 ml of 1-methyl-2-pyrrolidinone at 115° C. is added 3 g of 3-acetamido-pyrrolidine. After stirring at 100° C. for 20 hours, the solvent is removed by reduced pressure to dryness. Ethanol is added to the residue and washed with ether and then diluted cold hydrochloric acid and then water. The solid is dried, yielding 1.60 g 1-phenyl-6-fluoro-1,4-dihydro-4-oxo-7-(3-acetamido-1-pyrrolidinyl)-quinoline-3-carboxylic acid (9)

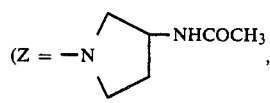

R-phenyl).

(b) The above product is then hydrolyzed with hydrochloric acid at 80° C. to give 1-phenyl-6-fluoro-1,4-dihydro-4-oxo-7-(3-amino-1-pyrrolidinyl)quinoline-3-carboxylic acid (9)

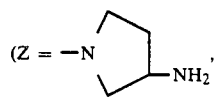

R=phenyl) hydrochloride salt.

EXAMPLE 33

1-p-fluorophenyl-6-fluoro-1,4-dihydro-4-oxo-7-(3-amino-1-pyrrolidinyl)quinoline-3-carboxylic acid In the described fashion as Example 32, replacing the 7-chloro-1-phenyl-6-fluoro-1,4-dihydro-4-oxo-quinoline-3-carboxylic acid with 7-chloro-1-p-fluorophenyl-6-fluoro-1,4-dihydro-4-oxo-quinoline-3-carboxylic acid (product of Example 4(b)) one can obtain the 1-p-fluorophenyl-6-fluoro-1,4-dihydro-4-oxo-7-(3-amino-1-pyrrolidinyl)quinoline-3-carboxylic acid hydrochloride salt (9)

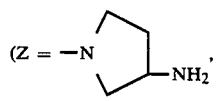

R=p-fluorophenyl) in good yield.

EXAMPLE 34

1-p-hydroxyphenyl-6-fluoro-1,4-dihydro-4-oxo-7-(3-amino-1-pyrrolidinyl)quinoline-3-carboxylic acid In the described fashion as Example 32, replacing the 7-chloro-1-phenyl-6-fluoro-1,4-dihydro-4-oxo-quinoline-3-carboxylic acid with 7-chloro-1-p-hydroxyphenyl-6-fluoro-1,4-dihydro-4-oxo-quinoline-3-carboxylic acid (product of Example 12(b)) one can obtain the 1-p-hydroxyphenyl-6-fluoro-1,4-dihydro-4-oxo-7-(3-amino-1-pyrrolidinyl)quinoline-3-carboxylic acid hydrochloride salt (9)

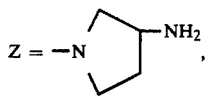

R=p-hydroxyphenyl) in good yield.

EXAMPLE 35

1-(2,4-difluorophenyl)-6-fluoro-1,4-dihydro-4-oxo-7-(3-amino-1-pyrrolidinyl)quinoline-3-carboxylic acid In the described fashion as Example 32, replacing the 7-chloro-1-phenyl-6-fluoro-1,4-dihydro-4-oxo-quinoline-3-carboxylic acid with 7-chloro-1-(2,4-difluorophenyl)-6-fluoro-1,4-dihydro-4-oxo-quinoline-3-carboxylic acid (product of Example 6(b)) one can obtain the 1-(2,4-difluorophenyl)-6-fluoro-1,4-dihydro-4-oxo-7-(3-amino-1-pyrrolidinyl)-quinoline-3-carboxylic acid and its hydrochloride salt (9)

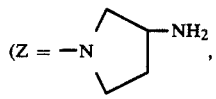

R=2,4-difluorophenyl).

EXAMPLE 36

1-p-fluorophenyl-6-fluoro-1,4-dihydro-4-oxo-7-(3-amino-4-methyl-1-pyrrolidinyl)quinoline-3-carboxylic acid The procedure of Example 25 can be repeated, replacing thiomorpholine with 3-amino-4-methyl-1-pyrrolidine to obtain 1-p-fluorophenyl-6-fluoro-1,4-dihydro-4-oxo-7-(3-amino-4-methyl-1-pyrrolidinyl)quinoline-3-carboxylic acid and its hydrochloride salt (9)

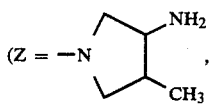

R-4-fluorophenyl).

EXAMPLE 37

1-(2,4-difluorophenyl)-6-fluoro-1,4-dihydro-4-oxo-7-(3-amino-4-methyl-1-pyrrolidinyl)-quinoline-3-carboxylic acid The procedure of Example 25 can be repeated, replacing thiomorpholine with 3-amino-4-methyl-1-pyrrolidine and also 7-chloro-1-p-fluorophenyl-6-fluoro-1,4-dihydro-4-oxo-quinoline-3-carboxylic acid with 7-chloro-1-(2,4-difluorophenyl)-6-fluoro-1,4-dihydro-4-oxo-quinoline-3-carboxylic acid (product of Example 6(b)) to obtain 1-(2,4-difluorophenyl)-6-fluoro-1,4-dihydro-4-oxo-7-(3-amino-4-methyl-1-pyrrolidinyl)-quinoline-3-carboxylic acid (9)

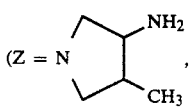

R=2,4-difluorophenyl).

EXAMPLE 38

1-p-fluorophenyl-6-fluoro-1,4-dihydro-4-oxo-7-(cis-3-aminomethyl-4-chloro-1-pyrrolidinyl)quinoline-3-carboxylic acid (a) The procedure of Example 25 can be repeated, replacing 3-thiomorpholine with cis-3-acetamidomethyl-4-chloro-1-pyrrolidine to obtain 1-p-fluorophenyl-6-fluoro-1,4-dihydro-4-oxo-7-(cis-3-acetamido-methyl-4-chloro-1-pyrrolidinyl)quinoline-3-carboxylic acid (9)

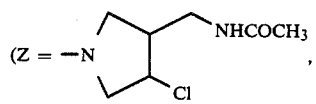

R=4-fluorophenyl).

(b) The above product is then hydrolyzed with hydrochloric acid at 80° C. to give 1-p-fluorophenyl-6-fluoro-1,4-dihydro-4-oxo-7-(cis-3-aminomethyl-4-chloro-1-pyrrolidinyl)quinoline-3-carboxylic acid (9)

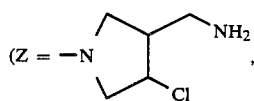

R=4-fluorophenyl)

EXAMPLE 39

1-(2,4-difluorophenyl)-6-fluoro-1,4-dihydro-4-oxo-7-(cis-3-aminomethyl-4-chloro-1-pyrrolidinyl)quinoline-3-carboxylic acid Following the procedure as described in Example 38, replacing 7-chloro-1-p-fluorophenyl-6-fluoro-1,4-dihydro-4-oxo-quinoline-3-carboxylic acid with 7-chloro-1-(2,4-difluorophenyl)-6-fluoro-1,4-dihydro-4-oxo-quinoline-3-carboxylic acid (product of Example 6(b)) one can obtain 1-(2,4-difluorophenyl)-6-fluoro-1,4-dihydro-4-oxo-7-(cis-3-aminomethyl-4-chloro-1-pyrrolidinyl)-quinoline-3-carboxylic acid (9)

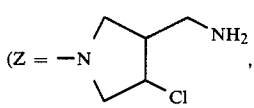

R=2,4-difluorophenyl).

EXAMPLE 40

1-p-fluorophenyl-6-fluoro-1,4-dihydro-4-oxo-7-(3-methyl-1-piperazinyl)quinoline-3-carboxylic acid The procedure of Example 25 can be repeated, replacing thiomorpholine with 2-methylpiperazine to obtain 1-p-fluorophenyl-6-fluoro-1,4-dihydro-4-oxo-7-(3-methyl-1-piperazinyl)quinoline-3-carboxylic acid (9)

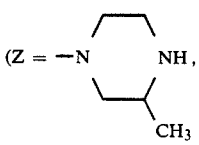

R=p-fluorophenyl).

EXAMPLE 41

1-(2,4-difluorophenyl)-6-fluoro-1,4-dihydro-4-oxo-7-(3-methyl-1-piperazinyl-quinoline-3-carboxylic acid Following the procedure described in Example 40, replacing 7-chloro-1-p-fluorophenyl-6-fluoro-1,4-dihydro-4-oxo-quinoline-3-carboxylic acid with 7-chloro-1-(2,4-difluorophenyl)-6-fluoro-1,4-dihydro-4-oxo-quinoline-3-carboxylic acid (product of Example 6(b)) one can obtain 1-(2,4-difluorophenyl)-6-fluoro-1,4-dihydro-4-oxo-7-(3-methyl-1-piperazinyl)quinoline-3-carboxylic acid (9)

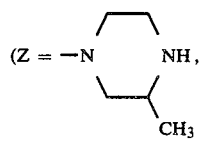

R-2,4-difluorophenyl).

EXAMPLE 42

1-p-fluorophenyl-6-fluoro-1,4-dihydro-4-oxo-7-(3-ethylaminomethyl-1-pyrrolidinyl)quinoline-3-carboxylic acid The procedure of Example 38 can be repeated, replacing cis-3-acetamidomethyl-4-chloro-1-pyrrolidine with 3-N-ethylacetamidomethyl-1-pyrrolidine to obtain 1-p-fluorophenyl-6-fluoro-1,4-dihydro-4-oxo-7-(3-ethylaminomethyl-1-pyrrolidinyl)quinoline-3-carboxylic acid (9)

(Z = —N⟨⟩—CH₂—NHC₂H₅),

R=p-fluorophenyl).

EXAMPLE 43

1-(2,4-difluorophenyl)-6-fluoro-1,4-dihydro-4-oxo-7-(3-ethylaminomethyl-1-pyrrolidinyl)quinoline-3-carboxylic acid Following the procedure described in Example 42 can be repeated, replacing 7-chloro-1-p-fluorophenyl-6-fluoro-1,4-dihydro-4-oxo-quinoline-3-carboxylic acid with 7-chloro-1-(2,4-difluorophenyl)-6-fluoro-1,4-dihydro-4-oxo-quinoline-3-carboxylic acid (product of Example 6(b)) one can obtain 1-(2,4-difluorophenyl)-6-fluoro-1,4-dihydro-4-oxo-7-(3-ethylaminomethyl-1-pyrrolidinyl)quinoline-3-carboxylic acid (9)

(Z = —N⟨⟩—CH₂—NHC₂H₅),

R=2,4-difluorophenyl).

EXAMPLE 44

In similar fashion as Example 29, the use of various 1-aryl-7-chloro-6-fluoro-1,4-dihydro-4-oxo-quinoline-3-carboxylic acids (7), wherein aryl represents R, in place of 7-chloro-1-phenyl-6-fluoro-1,4-dihydro-4-oxo-quinoline-3-carboxylic acid (7) (R-phenyl) and the use of appropriate substituted amines in place of morpholine, the following additional compounds (9) can be made as summarized in Table III.

TABLE III

| | Norpholine Replacement | Acid (7) R₆ = H  R | Compound (9) Obtained Z | R |
|---|---|---|---|---|
| 1. | ethylamine | phenyl | —NHC₂H₅ | phenyl |
| 2. | ethylamine | p-fluorophenyl | —NHC₂H₅ | p-fluorophenyl |
| 3. | methylamine | p-fluorophenyl | —NHCH₃ | p-fluorophenyl |
| 4. | methylamine | p-hydroxyphenyl | —NHCH₃ | hydroxyphenyl |
| 5. | dimethylamine | p-fluorophenyl | —N(CH₃)₂ | p-fluorophenyl |
| 6. | diethylamine | p-hydroxyphenyl | —N(C₂H₅)₂ | p-hydroxyphenyl |
| 7. | hydrazine | phenyl | —NHNH₂ | phenyl |
| 8. | N—methylhydrazine | p-fluorophenyl | —NCH₃NH₂ | p-fluorophenyl |
| 9. | 3-hydroxypyrrolidine | phenyl | —N⟨⟩—OH | phenyl |
| 10. | 3-hydroxypyrrolidine | p-fluorophenyl | —N⟨⟩—OH | p-fluorophenyl |
| 11. | 3-hydroxypyrrolidine | p-hydroxyphenyl | —N⟨⟩—OH | p-hydroxyphenyl |
| 12. | 3-hydroxypyrrolidine | p-methylphenyl | —N⟨⟩—OH | p-methylphenyl |

TABLE III-continued

| Norpholine Replacement | Acid (7) $R_6$ = H R | Compound (9) Obtained Z | R |
|---|---|---|---|
| 13. pyrrolidine | phenyl |  | phenyl |
| 14. pyrrolidine | p-fluorophenyl |  | p-fluorophenyl |
| 15. pyrrolidine | p-hydroxyphenyl |  | p-hydroxyphenyl |
| 16. pyrrolidine | o-fluorophenyl |  | o-fluorophenyl |
| 17. piperidine | phenyl |  | phenyl |
| 18. piperidine | p-fluorophenyl |  | p-fluorophenyl |
| 19. piperidine | p-hydroxyphenyl |  | p-hydroxyphenyl |
| 20. piperidine | 4-pyridinyl |  | 4-pyridinyl |
| 21. piperidine | 3-furyl |  | 3-furyl |
| 22. N—(2-hydroxyethylamine) | p-fluorophenyl | —N—CH$_2$CH$_2$OH | p-fluorophenyl |
| 23. pyrrolidine | 2,4-difluorophenyl |  | 2,3-difluorophenyl |
| 24. pyrrolidine | 2-hydroxy-4-fluorophenyl |  | 2-hydroxy-4-fluorophenyl |
| 25. pyrrolidine | 4-hydroxy-2-fluorophenyl |  | 4-hydroxy-2-fluorophenyl |
| 26. 4-acetylpiperazine | p-fluorophenyl |  | p-fluorophenyl |

TABLE III-continued

| Norpholine Replacement | Acid (7) $R_6$ = H | | Compound (9) Obtained | |
|---|---|---|---|---|
| | R | Z | | R |
| 27. 4-propionyl | p-fluorophenyl | 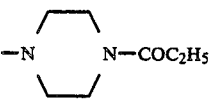 | | p-fluorophenyl |

It will be understood that various changes and modifications can be made in the details of procedure, formulation and use without departing from the spirit of the invention, especially as defined in the following claims.

What is claimed is:

1. A compound having the formula:

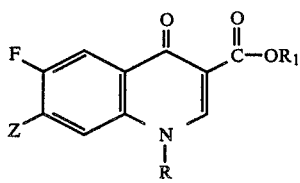

wherein $R_1$ is hydrogen or a carboxy protecting group; R is selected from the group consisting of (1) an aromatic heterocyclic ring having 5 to 6 atoms therein, with 1 to 2 hetero atoms being selected from the group consisting of S, O and N and the remaining atoms in the ring being carbon atoms and substituted derivatives of said aromatic heterocyclic ring wherein the aromatic heterocyclic ring is mono-substituted with $C_1$ to $C_6$ alkyl; and (2) a phenyl group having the formula:

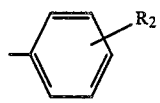

wherein $R_2$ is one, two or three substituents independently selected from the group consisting of hydrogen, halogen, cyano, $C_1$ to $C_6$ alkyl, halo-substituted $C_1$ to $C_6$ alkyl, a group having the formula:

wherein —Y— is —O— or —S— or $R_3$ is hydrogen or $C_1$ to $C_6$ alkyl, and $NH_2$; and Z is selected from the group consisting of (1) an aliphatic heterocyclic ring having the structure:

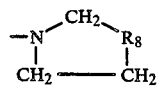

wherein $R_8$ is $CH_2$, $(CH_2)_2$ or a group of the formula —$(CH_2)_n$—$R_9$— wherein $R_9$ is —N—, —O—, or —S— and n is 0, 1 or 2, and substituted derivatives thereof wherein the aliphatic heterocyclic ring is substituted with one, two or three substituents independently selected from the group consisting of $C_1$ to $C_6$ alkyl, $C_1$ to $C_3$ alkylamino-substituted $C_1$ to $C_6$ alkyl, amino-substituted $C_1$ to $C_6$ alkyl, hydroxy, alkanoyl having 1 to 6 carbon atoms, alkanoylamido having 1 to 6 carbon atoms, halogen, an amine of the formula:

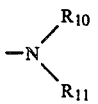

wherein $R_{10}$ and $R_{11}$ are each independently selected from the group consisting of hydrogen and $C_1$ to $C_6$ alkyl; and (2) an amino group of the formula:

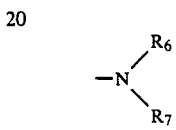

wherein $R_6$ is hydrogen or $C_1$ to $C_6$ alkyl, and $R_7$ is selected from the group consisting of $C_1$ to $C_6$ alkyl, $NH_2$, a mono-($C_1$ to $C_4$) alkylamino group and a di-($C_1$ to $C_4$) alkylamino group, and pharmaceutically acceptable salts thereof.

2. A compound as defined in claim 1 wherein the aliphatic heterocyclic ring is selected from the group consisting of piperazinyl groups, piperidinyl groups, pyrrolidinyl groups, morpholino groups, thiomorpholino groups and homopiperazinyl groups and substituted derivatives thereof.

3. A compound as defined in claim 1 wherein the aromatic heterocyclic group is selected from the group consisting of pyridyl, pyrazinyl, thiazoyl, furyl, thienyl.

4. A compound as defined in claim 1 wherein $R_1$ is hydrogen.

5. A compound as defined in claim 1 wherein Z is an amino group having the formula:

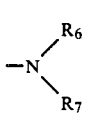

wherein $R_6$ is hydrogen or $C_1$ to $C_6$ alkyl, and $R_7$ is $C_1$ to $C_6$ alkyl, $NH_2$, a mono-($C_1$ to $C_4$) alkylamino group or a di-($C_1$ to $C_4$) alkylamino group.

6. A compound having the formula:

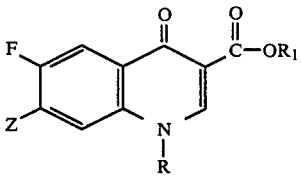

wherein Z is (1) mono- or di-substituted pyrrolidinyl wherein the substituent is independently selected from $NH_2$, $C_1$ to $C_3$ alkyl, halogen, amino-substituted $C_1$ to $C_6$ alkyl and $C_1$ to $C_3$ alkylamino-substituted $C_1$ to $C_6$ alkyl, or (2) piperazinyl or substituted piperazinyl wherein the piperazinyl ring is substituted with one, two or three substituents independently selected from $C_1$ to $C_6$ alkyl, or $C_1$ to $C_6$ alkanoyl; $R_1$ is hydrogen or a carboxy protecting group, and R is phenyl or substituted phenyl wherein the phenyl ring is substituted with one, two or three substituents independently selected from $C_1$ to $C_6$ alkyl, halogen, methylenedioxy and hydroxy and pharmaceutically acceptable salts thereof.

7. A compound as defined in claim 6 wherein R is phenyl, Z is piperazinyl and $R_1$ is hydrogen.

8. A compound as defined in claim 6 wherein R is phenyl, Z is 4-methylpiperazinyl and $R_1$ is hydrogen.

9. A compound as defined in claim 6 wherein R is p-fluorophenyl, Z is piperazinyl and $R_1$ is hydrogen.

10. A compound as defined in claim 6 wherein R is p-fluorophenyl, Z is 4-methyl-1-piperazinyl and $R_1$ is hydrogen.

11. A compound as defined in claim 6 wherein R is p-fluorophenyl, Z is 3-methyl-1-piperazinyl and $R_1$ is hydrogen.

12. A compound as defined in claim 6 wherein R is p-fluorophenyl, Z is 3-amino-1-pyrrolidinyl and $R_1$ is hydrogen.

13. A compound as defined in claim 6 wherein Z is 3-amino-4-methyl-1-pyrrolidinyl, R is p-fluorophenyl and $R_1$ is hydrogen.

14. A compound as defined in claim 6 wherein Z is cis-3-aminomethyl-4-chloro-1-pyrrolidinyl, R is p-fluorophenyl and $R_1$ is hydrogen.

15. A compound as defined in claim 6 wherein Z is 3-ethylaminomethyl-1-pyrrolidinyl, R is p-fluorophenyl and $R_1$ is hydrogen.

16. A compound as defined in claim 6 wherein Z is piperazinyl, R is 2,4-difluorophenyl and $R_1$ is hydrogen.

17. A compound as defined in claim 6 wherein Z is 4-methyl-1-piperazinyl, R is 2,4-difluorophenyl and $R_1$ is hydrogen.

18. A compound as defined in claim 6 wherein Z is 3-methyl-1-piperazinyl, R is 2,4-difluorophenyl and $R_1$ is hydrogen.

19. A compound as defined in claim 6 wherein Z is 3-amino-1-pyrrolidinyl, R is 2,4-difluorophenyl and $R_1$ is hydrogen.

20. A compound as defined in claim 6 wherein Z is 3-amino-4-methyl-1-pyrrolidinyl, R is 2,4-difluorophenyl and $R_1$ is hydrogen.

21. A compound as defined in claim 6 wherein Z is cis-3-aminomethyl-4-chloro-1-pyrrolidinyl, R is 2,4-difluorophenyl and $R_1$ is hydrogen.

22. A composition having antibacterial activity in pharmaceutical dosage form containing a diluent and a compound as defined in claim 1.

23. A composition having antibacterial activity in pharmaceutical dosage form containing a diluent and a compound as defined in claim 6.

24. A method of treating a bacterial infection in a patient comprising administering to a patient in need a therapeutically effective amount of a compound as defined in claim 1.

25. A method of treating a bacterial infection in a patient comprising administering to a patient in need a therapeutically effective amount of a compound as defined in claim 6.

* * * * *

UNITED STATES PATENT AND TRADEMARK OFFICE
CERTIFICATE OF CORRECTION

PATENT NO. : 4,730,000
DATED : March 8, 1988
INVENTOR(S) : Daniel Chu

It is certified that error appears in the above-identified patent and that said Letters Patent is hereby corrected as shown below:

In Column 2, Line 59, delete "piperazinyl groups,".

In Column 9, Line 38, delete "p-perazine", substitute therefor, "piperazine".

In Column 11, Line 3, delete "(p-difluorophenyl)", substitute therefor, "(p-fluorophenyl)".

In Column 11, Line 18, following "p-fluorophenyl" insert ")".

In Column 11, Line 21, following "(2,4-difluorophenyl" insert ")".

In Column 27, Line 49 the word "or", second occurrence, should read "and".

Signed and Sealed this

Eighteenth Day of October, 1988

Attest:

DONALD J. QUIGG

*Attesting Officer*  *Commissioner of Patents and Trademarks*

UNITED STATES PATENT AND TRADEMARK OFFICE

CERTIFICATE EXTENDING PATENT TERM
UNDER 35 U.S.C. § 156

PATENT NO.:     4,730,000

DATED:          March 8, 1988

INVENTOR:       Daniel T. Chu

PATENT OWNER:   Abbott Laboratories

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

328 DAYS with all rights pertaining thereto as provided by 35 U.S.C. § 156(b).

I have caused the seal of the Patent and Trademark Office to be affixed this 20th day of May 1993.

Michael K. Kirk
Acting Commissioner of Patents and Trademarks